United States Patent [19]

Furlan

[11] Patent Number: 4,965,382
[45] Date of Patent: Oct. 23, 1990

[54] BISMUTH-CONTAINING COMPOSITIONS SUITABLE FOR THERAPEUTIC USE

[75] Inventor: Diego Furlan, Segrate S. Felice, Italy

[73] Assignee: Eurosearch S.r.l., Milan, Italy

[21] Appl. No.: 466,764

[22] Filed: Jan. 18, 1990

[30] Foreign Application Priority Data

Jan. 25, 1989 [IT]  Italy ................................ 19172 A/89

[51] Int. Cl.$^5$ .......................... C07F 9/94; C07F 1/06; A61K 31/29
[52] U.S. Cl. ........................................ 556/79; 556/77; 514/926
[58] Field of Search ................... 556/79, 77; 514/926, 514/925, 784, 667

[56] References Cited

U.S. PATENT DOCUMENTS

| | | | |
|---|---|---|---|
| 1,536,711 | 5/1925 | Hahl ........................................ | 556/77 |
| 1,663,201 | 3/1928 | Kober ..................................... | 556/79 |
| 2,054,731 | 9/1936 | Pyman et al. ...................... | 556/79 X |
| 2,232,411 | 2/1941 | Sondern et al. ....................... | 556/79 |
| 2,348,984 | 5/1944 | Lehman et al. ....................... | 556/77 |
| 3,840,575 | 10/1974 | MacClaren ............................ | 556/78 |
| 4,016,268 | 4/1977 | Goldenberg et al. .......... | 514/925 X |

*Primary Examiner*—Arthur C. Prescott
*Attorney, Agent, or Firm*—Birch, Stewart, Kolasch & Birch

[57] ABSTRACT

A bismuth-containing product in the form of a powder easily dispersible in water to form a colloidal solution suitable for oral administration as an antiulcer drug is obtained from an aqueous solution of potassium citrate, bismuth citrate and potassium hydroxide, the product being precipitated from the aqueous solution by dilution with acetone.

2 Claims, No Drawings

BISMUTH-CONTAINING COMPOSITIONS SUITABLE FOR THERAPEUTIC USE

This invention relates to the preparation of a bismuth-based product useful as a drug for oral administration in peptic ulcer therapy.

Said product is of solid powder form and is easily dispersed in water to form a stable colloidal solution.

GB patent 1,478,742 describes the preparation of a solid composition in powder form obtained by spray-drying an aqueous colloidal solution containing bismuth citrate, a polyhydroxy alcohol, particularly saccharose, and ammonia. The presence of saccharose was considered necessary to produce a powder product easily dispersible in water at the time of use, to again form a stable colloidal solution.

The preparation process was complicated with regard to the spray drying because of the sugar presence which meant that low-temperature drying has to be used, and easily resulted in the formation of incrustation and deposits in the apparatus.

Furthermore, the presence of ammonia in the final product makes it unpleasant.

European patent 75992 describes an improved method in which the presence of sugar is eliminated in the colloidal bismuth citrate solution which is to be subjected to spray drying. The solution is prepared by adding considerable quantities of $NH_3$. $NH_3$ is present in the dried product in powder to the extent of 2–6% by weight.

The present invention provides a new process for preparing a bismuth-based composition starting from bismuth citrate, having the property of easy dispersal in aqueous liquids to form a colloidal solution with therapeutic antiulcer properties.

The process according to the present invention represents a very advantageous alternative to the processes of the known art based on spray-drying an aqueous mixture containing bismuth citrate, which requires a costly drying apparatus and often involves operational difficulties.

With the process according to the invention a new product based on a mixed bismuth and potassium citrate in the molar ratio of 1:1 is obtained in the form of a very finely powdered solid having the property of easy dispersal in water to form a stable colloidal solution. It is obtained by preparing an aqueous solution of K citrate and Bi citrate in a 1:1 molar ratio and by adding the minimum amount of KOH to obtain complete dissolving of the Bi citrate. The aqueous solution is then concentrated to a mixed citrate content of the order of 1.5 moles/l of mixed citrate. Acetone is then added to the aqueous solution to the extent of about 60 volumes per 100 volumes of solution under strong stirring, to precipitate the product in the form of a fine powder which is separated by filtration, washed with acetone and then dried at 70° C. under vacuum.

The product obtained consists substantially of the compound:

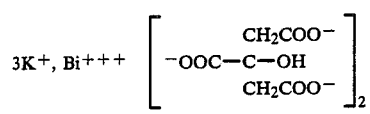

It has the property of easy dispersal in an aqueous liquid to form a colloidal solution of considerable therapeutic property in the treatment of the gastroduodenal ulcer.

The product according to the invention is used as active principle in pharmaceutical antiulcer compositions in combination with possible excipients and sweeteners, in the form of tablets, effervescent tablets, syrups etc.

An example of the preparation of the product according to the present invention is described by way of illustration only.

EXAMPLE 32.77 g of potassium citrate are dissolved in 200 ml of water at 60° C., 41.19 g of bismuth citrate are added, and KOH is then added under stirring, until the Bi citrate has completely dissolved (about 13 g of KOH).

The aqueous mixture is then concentrated under vacuum until it is reduced to one third of its initial volume. 40 ml of acetone are added to the cooled concentrated solution under strong stirring.

A milk-white precipitate appears in the form of an easily decantable fine powder.

This is filtered off, washed with acetone and then dried under vacuum at 70° C. The yield is quantitative.

On analysis, the product shows a Bi content as $Bi_2O_3$ of 33% by weight.

I claim:

1. A process for preparing from bismuth citrate a bismuth-based composition in the form of a fine powder easily dispersible in aqueous liquids with the formation of a colloidal solution having antiulcer therapeutic properties, consisting of dissolving equimolar quantities of potassium citrate and bismuth citrate in water and adding the minimum amount of KOH to obtain complete dissolution of the Bi citrate at 60° C., then concentrating the obtained aqueous solution by evaporation under vacuum until a mixed K and Bi citrate concentration of the order of 1.5 moles/l is obtained, and precipitating the product in the form of a fine powder by diluting the aqueous solution with acetone in a quantity of about 60 ml per 100 ml of solution, and finally separating the product by filtration, washing it with acetone, and drying it at 70° C. under vacuum.

2. A mixed potassium and bismuth citrate consisting of equimolar quantities of K citrate and Bi citrate, and being in the form of a fine powder easily dispersible in aqueous liquids to form a colloidal solution having therapeutic antiulcer properties.

* * * * *

UNITED STATES PATENT AND TRADEMARK OFFICE
CERTIFICATE OF CORRECTION

PATENT NO. : 4,965,382
DATED : October 23, 1990
INVENTOR(S) : Diego FURLAN It is certified that error appears in the above-identified patent and that said Letters Patent is hereby corrected as shown below:

Title page:

Column 1, change Assignee from "Eurosearch S.r.l." to

--Euroresearch S.r.l.--

Signed and Sealed this

Second Day of March, 1993

*Attest:*

STEPHEN G. KUNIN

*Attesting Officer*   Acting Commissioner of Patents and Trademarks